United States Patent [19]

Padden

[11] Patent Number: 5,145,729

[45] Date of Patent: Sep. 8, 1992

[54] COMPOSITE INTERMEDIATE BONDING STRUCTURES

[75] Inventor: James B. Padden, West Bloomfield, Mich.

[73] Assignee: Purolator Products Company, Tulsa, Okla.

[21] Appl. No.: 694,764

[22] Filed: May 2, 1991

Related U.S. Application Data

[62] Division of Ser. No. 457,304, Jan. 11, 1983, Pat. No. 5,076,875.

[51] Int. Cl.$^5$ .................... B32B 15/01; B32B 15/08; B32B 15/14

[52] U.S. Cl. .................... 428/220; 428/247; 428/251; 428/337; 428/594; 428/613; 428/615; 428/622

[58] Field of Search .............. 428/247, 251, 594, 613, 428/615, 622, 220, 337

[56] References Cited

U.S. PATENT DOCUMENTS 2,274,189  2/1942  Congleton .

Primary Examiner—James C. Cannon
Attorney, Agent, or Firm—Remy J. VanOphem

[57] ABSTRACT

A composite intermediate structure for joining two dissimilar materials together. The structure has a non-porous base with two bonding faces. A porous member is bonded to each of the faces. The base may be a metallic foil and the porous members may each be a metallic mesh.

22 Claims, 1 Drawing Sheet

COMPOSITE INTERMEDIATE BONDING STRUCTURES

This is a division of application Ser. No. 06/457,304, filed Jan. 11, 1983, now Pat. No. 5,076,875.

BACKGROUND OF THE INVENTION

1. Field of the Invention

The present invention is directed to composite intermediate bonding structures and, more particularly, to composite intermediate bonding structures for joining together dissimilar materials.

2. Description of the Prior Art

There are frequent occurrences where two dissimilar materials must be joined together. When this occurs, frequently the surfaces are incompatible since a common adhesive may not be available to properly bond to both surfaces. Furthermore, in some circumstances, the material of one of the elements to be bonded together is more suitable to bonding by a heat melt process or by use of a solvent. Additionally, even where there is a method of bonding the two dissimilar elements together, the bonding method is usually a compromise and, therefore, the bond produced is not extremely strong and may be subject to deterioration with time.

One method which has been proposed in the past for bonding dissimilar articles is described in U.S. Pat. No. 4,273,827 (issued Jun. 16, 1981). The adhesive assembly therein described contains a first adhesive and a second adhesive which is of a different strength or chemical composition than the first adhesive. Positioned between the first and second adhesives is a barrier for preventing contamination of the respective adhesives or the substrate to which they adhere. The combination of adhesives includes a spongy or foam layer. At least one of the adhesives is encapsulated or retained in bubbles of a plastic film and is released by pressing the adhesive assembly against one of the substrates.

While this adhesive assembly is suitable for use with certain adhesives which may be readily encapsulated in bubbles of a plastic film, each adhesive assembly manufactured in the manner described therein is suitable for only certain substrate materials. Furthermore, certain adhesives cannot be encapsulated in this form and certain other techniques of bonding cannot be applied, such as the use of solvents or heat melting, to bond two dissimilar materials when using the adhesive assembly described therein.

What is needed, therefore, is an intermediate composite bonding structure which may be used with each of the various bonding methods, such as those involving heat melting, solvents, and adhesives. Furthermore, it would be useful if such a structure could be manufactured inexpensively. It would also be useful if such a structure could be easily adapted for use with several dissimilar materials.

A bonding method which is known in the orthodontic industry is described in U.S. Pat. No. 4,068,379, issued Jan. 17, 1978. This technology involves brazing or spot welding foil to a machined orthodontic bracket and diffusion bonding metallic mesh to the foil. The mesh is then adhesively bonded to the side of the tooth. This method works well for joining a metallic structure to the tooth, but in general still does not provide a method for joining any two dissimilar materials.

The purpose of the present invention, therefore, is to provide an intermediate composite bonding structure having two bonding faces separated by a non-porous base wherein the individual bonding faces may be bonded to elements having dissimilar materials to thereby join these elements together.

SUMMARY OF THE INVENTION

The present invention provides a composite intermediate structure for joining together two elements of dissimilar materials.

The structure has a non-porous base with two bonding faces. Two porous members are provided, each being bonded to one of the faces. Each of the faces may, therefore, be bonded to one of the two dissimilar elements using adhesives, solvents, or heat melting.

In the preferred embodiment, the intermediate composite structure includes a thin metallic foil base. Each of the porous members consists of at least one layer of metallic mesh that is diffusion bonded to the foil. The mesh is preferably selected from one of the following size ranges:

$30 \times 30 \times 0.0065$;

$80 \times 80 \times 0.0037$;

$42 \times 42 \times 0.0055$; and $58 \times 58 \times 0.0045$

The principal object of the present invention is to provide an intermediate composite bonding structure for bonding together two dissimilar materials.

A further object of the present invention is to provide an intermediate composite bonding structure which may be inexpensively manufactured and which produces a permanent strong, reliable bond between two dissimilar structures.

Still another object of the present invention is to provide an intermediate composite bonding structure which is suitable for a wide range of bonding applications including adhesive bonding, heat melting, and bonding by the use of solvents.

Another object of the present invention is to provide an intermediate composite bonding structure which may be used to shield electronic components from corrosive electrolytic reactions.

Still another object of the present invention is to provide an intermediate composite bonding structure for bonding dissimilar elements, where each of the elements is chosen from a group consisting of ceramics, stainless steel, polyethylene, tetrafluoroethylene, rubber, polyvinyl chloride and bone.

These and other objects, features, and advantages of the present invention will become apparent to one skilled in the art when the following detailed description of the preferred embodiment is read in conjunction with the attached drawings wherein like reference numerals refer to like components throughout.

DETAILED DESCRIPTION OF THE PREFERRED EMBODIMENT

Figure 1:
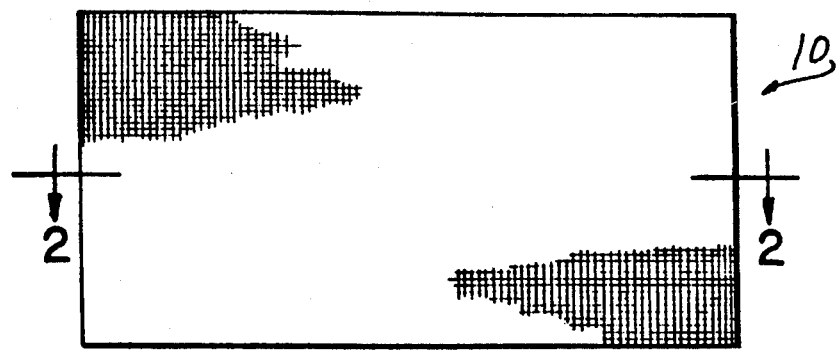
FIG. 1 is a top view of an example of a bonding structure according to the present invention.
Figure 2:
FIG. 2 is a cross-sectional view taken along line 2—2 of FIG. 1.

An example of an intermediate composite bonding structure according to the present invention is generally shown in the drawing and indicated by reference numeral 10.

The bonding structure or pad 10 has a non-porous base 12, in the example illustrated, consisting of a thin layer of film. The base 12 is selected so as to be non-porous relative to any adhesive, solvent, or melted material encountered in the bonding process, as described below in greater detail. In the preferred embodiment, the base 12 is a thin layer of metallic foil having a thickness, shown in FIG. 4 by reference character B, ranging from two thousandths of an inch (0.002 in.) to thirty thousandths of an inch (0.030 in.). The foil may be, if desired, a corrosion resistant material such as stainless steel. Alternate corrosion resistant materials which may be suitable for different applications include Monel[2], nickel, copper, or other nickel based or super alloy metals, well known in the art.

The base 12 is provided with two bonding faces 14 and 16. Porous members or meshes 18 or 20 are bonded to each of the bonding faces 14 or 16, respectively. The thickness of each porous member 18 and 20, shown in the drawing by reference characters C and D respectively, ranges from six thousandths of an inch (0.006 in.) to twelve thousandths of an inch (0.012 in.) in the preferred embodiment.

Figure 3:
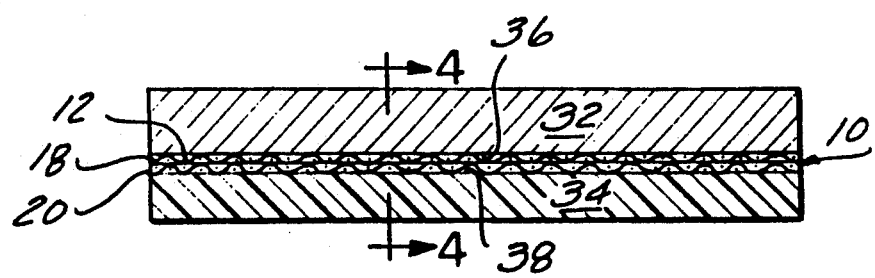
FIG. 3 is a side view of the intermediate composite bonding structure of FIG. 1 in use, placed between two dissimilar elements to be joined.
Figure 4:
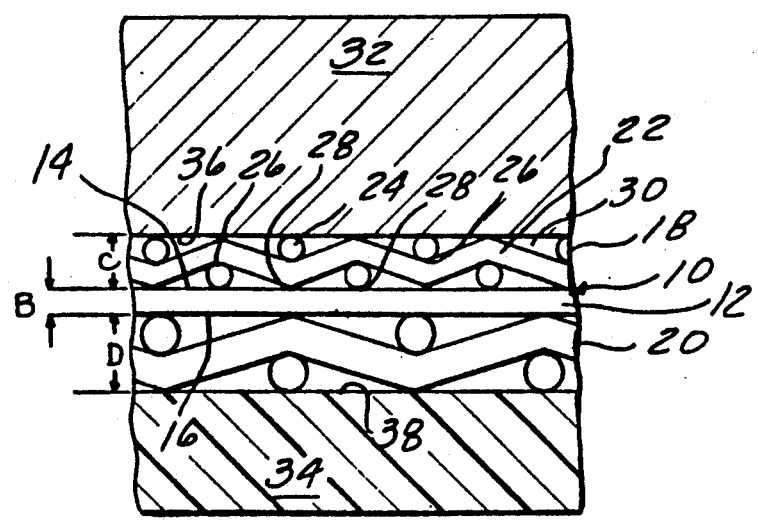
FIG. 4 is an enlarged sectional view taken along line 4—4 of FIG. 3.

In the preferred embodiment, each of the porous members consists of at least one layer of wire mesh. For example, the porous member 18 consists of a mesh formed of woven wires including wires 22 oriented parallel to the plane of the drawing as shown in FIGS. 3 and 4, and wires 24 generally oriented perpendicular to the plane of view of FIGS. 3 and 4. The wire mesh may be brazed, sintered or diffusion bonded to the foil or base 12 in a manner similar to that described in U.S. Pat. No. 4,068,379, referred to in the background of the present invention. The mesh count and wire size of the porous members or meshes 18 and 20 may be chosen for a particular type of material to be bonded to the respective face 14 or 16 of the bonding structure or pad 10. Examples of mesh sizes are described later herein.

As best shown in FIG. 4, the individual wires 22 and 24 are bonded together at cross points 26. Each of the wires 22 and 24 are also bonded to the base 12 at bond points 28. An air space 30 exists in the mesh for absorption, as described later herein, of adhesives, solvents, or melted or dissolved material.

As best shown in FIGS. 3 and 4, dissimilar elements 32 and 34 may be joined together by joining each element 32 and 34 to one bonding face 14 or 16 of the intermediate bonding structure 10. For example, when an adhesive is to be used, the adhesive may be applied to the porous member or mesh 18 and/or to a surface 36 of the element 32 to be bonded thereto. Pressure is applied between the bonding structure 10 and the element 32 to be bonded to form a tight, strong adhesive bond therebetween. The adhesive used will flow partly into the air space 30 in the mesh thereby providing a strong, mechanical bond between the adhesive and the bonding structure 10.

For example, if the element 32 is formed of a ceramic material, an epoxy type of adhesive may be appropriate. When epoxy adhesive is used, the mesh 18 preferably is $30 \times 30 \times 0.0065$. That is, the mesh preferably consists of wire having a diameter of sixty five ten thousandths of an inch (0.0065 in.) and having thirty (30) wires 22 and thirty (30) wires 24 in a square inch of mesh. Alternatively, quick setting adhesive, such as cyanoacrylates, may be used for the adhesion of a ceramic material but with a smaller sized mesh such as $80 \times 80 \times 0.0037$.

If, for example, the element 32 is made of stainless steel, the adhesive may be epoxy and the mesh size may be $30 \times 30 \times 0.0065$, as is used for ceramic. Alternatively, stainless steel may be bonded by using synthetic rubber adhesive using a mesh of size $42 \times 42 \times 0.0055$.

As a third example, the element 32 to be bonded is formed of rubber, and an appropriate adhesive would be rubber cement and a suitable mesh size would be $42 \times 42 \times 0.0055$.

It should be readily apparent to those skilled in the art that other materials, adhesives, and mesh sizes would be appropriate for other purposes. The mesh size chosen to use with an adhesive is chosen on the basis of the viscosity of the adhesive, rather than the properties of the material of the element 32. When using this method to bond a polyvinyl chloride element to the bonding structure, the appropriate mesh size is $58 \times 58 \times 0.0045$.

Alternatively, other methods may be used for bonding the surfaces 36 and 38 of the elements 32 and 34, respectively, to the bonding structure or pad 10. For example, a polyvinyl chloride may be readily bonded to the wire mesh 18 or 20 by the application of a solvent to the surface 36 or 38 of the element 32 or 34. The solvent temporarily dissolves a portion of the polyvinyl chloride, which portion flows into the interstitial spaces 30 in the mesh and, subsequently, hardens therein to bond the elements 32 and 34 to the bonding structure 10.

Still another method of bonding an element 32 or 34 to the wire mesh 18 or 20 is appropriate when bonding certain plastics, such as polyethylene and polytetrafluoroethylene, to the bonding structure 10. These and similar plastics may be bonded to the wire mesh 18 or 20 of the bonding structure 10 by heating the surface 36 or 38 of the element 32 or 34, respectively, to be bonded, and pressing the surface against the wire mesh 18 or 20 so that the material at the surface flows into the interstitial spaces 30 in the porous member or mesh 18 or 20. Upon cooling, a strong, mechanical bond will be formed between the plastic element and the bonding structure 10. An appropriate mesh size for this application would be $30 \times 30 \times 0.0065$.

When one of the elements 32 or 34 to be bonded to the bonding structure 10 is bone, a multi-layered mesh, such as that disclosed in U.S. Pat. No. 4,068,379, described above, may be appropriate. Similarly, multiple layers of mesh may be included in other applications where one layer provides a bond of insufficient strength.

The composite bonding structure 10 may be produced, for varying applications having differing mesh sizes on the bonding faces 14 and 16 as described above. In the preferred embodiment, the mesh sizes are chosen from the four sizes described above. It may readily be appreciated, however, that alternate mesh sizes may be appropriate for some applications. Furthermore, other porous materials and structures other than the metallic mesh may be used for the porous members 18 and 20 such as metallic felt metal or sintered powdered metal for some applications. The mesh sizes chosen were selected on the basis of the viscosity of the adhesives, melted material, or dissolved material used and are selected from sizes which are currently known and available commercially.

It will be apparent, therefore, to one skilled in the art that the above described bonding structure 10 provides a convenient, inexpensive, and reliable intermediate structure for joining two dissimilar elements. The above description of the present invention is by way of example and not by way of limitation. Variations and modifications therefrom will be apparent to those skilled in the art and are intended to be included within the scope of the claims appended hereto.

What is claimed as novel is as follows:

1. A composite bonding structure comprising:
   a non-porous metallic sheet having a first bonding face and a second bonding face;
   a first porous metallic mesh member bonded to said first bonding face of said non-porous metallic sheet;
   a second porous metallic mesh member bonded to said second bonding face of said non-porous metallic sheet;
   means for bonding all contact points between said first bonding face of said non-porous metallic sheet and said first porous metallic mesh member; and
   means for bonding all contact points between said second bonding face of said non-porous metallic sheet and said second porous metallic mesh member.

2. The composite bonding structure of claim 1 wherein said non-porous metallic sheet is a thin and flat element having said first and second bonding faces oppositely disposed thereon.

3. The composite bonding structure of claim 2 wherein said non-porous metallic sheet is comprised of a sheet of metallic foil.

4. The composite bonding structure of claim 3 wherein said sheet of metallic foil is comprised of a corrosion resistant metallic material.

5. The composite bonding structure of claim 2 wherein said non-porous metallic sheet has a thickness between 0.002" and 0.030".

6. The composite bonding structure of claim 1 wherein said first and second porous metallic mesh members are diffusion bonded to said non-porous metallic sheet.

7. The composite bonding structure of claim 1 wherein said first and second porous metallic mesh members are approximately $30 \times 30 \times 0.0065''$.

8. The composite bonding structure of claim 1 wherein said first and second porous metallic mesh members are approximately $80 \times 80 \times 0.0037''$.

9. The composite bonding structure of claim 1 wherein said first and second porous metallic mesh members are approximately $42 \times 42 \times 0.0055''$.

10. The composite bonding structure of claim 1 wherein said first and second porous metallic mesh members are approximately $58 \times 58 \times 0.0045''$.

11. The composite bonding structure of claim 1 wherein said first and second porous metallic mesh members have a thickness of approximately 0.010".

12. The composite bonding structure of claim 1 wherein said base and each of said porous members is flexible.

13. A composite bonding structure for bonding a first element comprised of a first material and requiring a first adhesive to a second element comprised of a second material and requiring a second adhesive, said bonding structure comprising:
   a non-porous metallic sheet having a first bonding face and a second bonding face;
   a first porous metallic mesh member bonded to said first bonding face of said non-porous metallic sheet, said first porous metallic sheet member being permeable to said first adhesive;
   a second porous metallic mesh member bonded to said second bonding face of said non-porous metallic sheet, said second porous metallic mesh member being impermeable to said second adhesive;
   means for bonding all contact points between said first bonding face of said non-porous metallic sheet and said first porous metallic mesh member; and
   means for bonding all contact points between said second bonding face of said non-porous metallic sheet and said second porous metallic mesh member.

14. The composite bonding structure of claim 13 wherein said non-porous metallic sheet is comprised of a sheet of metallic foil.

15. The composite bonding structure of claim 13, wherein said first and second porous metallic mesh members are diffusion bonded to said non-porous metallic sheet.

16. The composite bonding structure of claim 13 wherein said first and second porous metallic mesh members are approximately $30 \times 30 \times 0.0065''$.

17. The composite bonding structure of claim 13 wherein said first and second porous metallic mesh members are approximately $80 \times 80 \times 0.0037''$.

18. The composite bonding structure of claim 13 wherein said first and second porous metallic mesh members are approximately $42 \times 42 \times 0.0055''$.

19. A composite bonding structure for bonding a first element comprised of a first material to a second element comprised of a second material, said bonding structure comprising:
   a thin flat non-porous metallic sheet having a first bonding face and a second bonding face disposed opposite said first bonding face;
   a first permeable metallic mesh bonded to said first bonding face;
   a second permeable metallic mesh bonded to said second bonding face;
   means for bonding said first bonding face of said thin flat non-porous metallic sheet to said first permeable metallic mesh; and
   means for bonding said second bonding face of said thin flat non-porous metallic sheet to said second permeable metallic mesh.

20. The composite bonding structure of claim 19 wherein said non-porous metallic sheet is comprised of a sheet of metallic foil.

21. The composite bonding structure of claim 20 wherein said non-porous metallic sheet has a thickness between 0.002" and 0.030".

22. The composite bonding structure of claim 21 wherein at least one of said first and second permeable metallic meshes is comprised of a metallic mesh material diffusion bonded to said thin flat non-porous metallic sheet.

* * * * *

UNITED STATES PATENT AND TRADEMARK OFFICE
CERTIFICATE OF CORRECTION

PATENT NO. : 5,145,729

DATED : September 8, 1992

INVENTOR(S) : James B. Padden

It is certified that error appears in the above-identified patent and that said Letters Patent is hereby corrected as shown below:

Column 3, line 21, delete "Monel$^2$" and insert -- Monel$^R$ --.

Signed and Sealed this

Nineteenth Day of October, 1993

Attest:

BRUCE LEHMAN

Attesting Officer

Commissioner of Patents and Trademarks